United States Patent [19]

Smith et al.

[11] 3,965,152

[45] *June 22, 1976

[54] PROCESS FOR PREPARING ALLYLIC ESTERS OF CARBOXYLIC ACIDS

[75] Inventors: William E. Smith, Schenectady; R. John Gerhart, Averill Park, both of N.Y.

[73] Assignee: General Electric Company, Pittsfield, Mass.

[ * ] Notice: The portion of the term of this patent subsequent to June 22, 1993, has been disclaimed.

[22] Filed: Feb. 4, 1974

[21] Appl. No.: 439,275

[52] U.S. Cl. ........................ 260/491; 260/410.9 N; 260/635 R
[51] Int. Cl.² ........................................ C07C 67/00
[58] Field of Search ................ 260/497 A, 410.9 N, 260/491, 632 C

[56] References Cited
UNITED STATES PATENTS

| | | | |
|---|---|---|---|
| 3,306,930 | 2/1967 | Copelin et al. | 260/497 A |
| 3,346,624 | 10/1967 | Schaeffer et al. | 260/497 A |
| 3,444,189 | 5/1969 | Olivier | 260/497 A |
| 3,668,257 | 6/1972 | Schaeffer | 260/497 A |

FOREIGN PATENTS OR APPLICATIONS

| | | | |
|---|---|---|---|
| 1,443,882 | 10/1968 | Germany | 260/497 A |
| 1,901,289 | 9/1970 | Germany | 260/497 A |

OTHER PUBLICATIONS

Boutry et al., Jour. of Catalysis, 23, pp. 19–30, (1971).

*Primary Examiner*—Lorraine A. Weinberger
*Assistant Examiner*—Michael Shippen
*Attorney, Agent, or Firm*—Donald M. Papuga; William F. Mufatti

[57] ABSTRACT

A process for preparing allylic esters of carboxylic acids which comprises reacting a mixture of a lower alkyl carboxylate ester, water, and the corresponding carboxylic acid and alcohol with an olefin having an allylic carbon-hydrogen bond and oxygen in the presence of an oxidation catalyst.

4 Claims, No Drawings

PROCESS FOR PREPARING ALLYLIC ESTERS OF CARBOXYLIC ACIDS

This invention relates to a process for preparing allylic esters of carboxylic acids which comprises reacting a mixture of a lower alkyl carboxylate ester, water, and the corresponding carboxylic acid and alcohol with a olefin having an allylic carbon-hydrogen bond and oxygen in the presence of a catalyst comprising a Group VIII noble metal, or its salts, or its oxides, or mixtures thereof. This invention additionally relates to an improved process for preparing butanediol.

BACKGROUND OF THE INVENTION

Allylic esters of carboxylic acids have been prepared by a number of different methods. A useful method of preparing allyl acetate, for example, is by contacting propylene with a palladium catalyst in the presence of oxygen and acetic acid. This is illustrated by U.S. Pat. Nos. 3,190,912, 3,275,608 and 3,670,014 and South African Pat. No. 701,077, for example. Allyl acetate is useful as an intermediate for the manufacture of polymers, plasticizers and other valuable materials.

Butanediol has been prepared by a number of different methods as summarized in copendng applications A and B, Ser. Nos. 365,228 and 365,231, both of William E. Smith and both filed May 30, 1973 both now abandoned. Applications A and B are assigned to the same assignee as the present invention and are incorporated herein by reference.

DESCRIPTION OF THE INVENTION

It has been discovered that allylic esters of carboxylic acids may be prepared in a novel way, using a mixture of a lower alkyl carboxylate ester, water, and the corresponding carboxylic acid and alcohol with an olefin having an allylic carbon-hydrogen bond and oxygen under oxidation conditions.

An important object of this invention is to make possible an improved process for preparing butanediol from inexpensive starting materials as compared with the prior art, i.e., propylene, carbon monoxide, hydrogen and oxygen, by way of several intermediate steps, mediated by a lower alkyl carboxylate ester (methyl acetate in this process) which is not consumed in the overall reaction.

A primary object of the present invention concerns a process for preparing allylic esters of carboxylic acids which comprises reacting a mixture of a lower alkyl carboxylate ester, water and the corresponding carboxylic acid and alcohol with an olefin having an allylic carbon-hydrogen bond and oxygen in the presence of a catalyst comprising a Group VIII noble metal, or its salts, or its oxides, or mixtures thereof. Preferably, the lower alkyl carboxylate ester is methyl acetate.

As described, supra, a useful method of preparing allylic esters of carboxylic acids is by reaction of the appropriate olefin and carboxylic acid under oxidation conditions as illustrated, for the case of allyl acetate, in Equation 1.

If the allylic ester so produced is to be used in a subsequent process that involves liberation of the carboxylate moiety as part of another ester, then said ester can be hydrolyzed (equation 2) by methods known in the art to make available the carboxylic acid for recycle to the original oxidation.

As indicated in equation 2, however, the hydrolysis is an equilibrium process; isolation of the carboxylic acid requires repeated equilibrations and distillations and is thus inconvenient.

It has been discovered that the recycle can be performed with much greater efficiency by subjecting the alkyl carboxylate to hydrolysis and using the hydrolysis mixture itself (containing the carboxylic acid, alcohol, water and unconverted ester, preferably at equilibrium) directly in the oxidation step. The alcohol and ester present cause essentially no deleterious effects in the operation; they pass through unchanged and suitable for use in recycle or in a subsequent step.

The lower alkyl carboxylate esters may be employed in the instant invention are illustrated by the following structure:

wherein $R_1$ and $R_2$ can contain from one to about eight carbon atoms. The preferred lower alkyl carboxylate ester is methyl acetate.

The olefins which may be employed in the instant invention are those having an allylic carbon-hydrogen bond, as illustrated by the following structure:

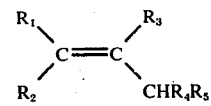

wherein $R_1$, $R_2$ and $R_3$ are independently selected from the group consisting of hydrogen, alkyl of 1–8 carbon atoms, aryl of 6–10 carbon atoms, aralkyl of 7 to 10 carbon atoms and the radical $—CHR_4R_5$, and wherein $R_4$ and $R_5$ are hydrogen, alkyl of 1–8 carbon atoms, aryl of 6–10 carbon atoms, and aralkyl of 7 to 10 carbon atoms. Preferred olefins are propylene and isobutylene.

The oxidation catalyst comprises a Group VIII noble metal, or its salts, or its oxides, or mixtures thereof. Specific examples of such catalysts include metals such as palladium, ruthenium, rhodium, platinum, osmium, and iridium as well as oxides and salts such as palladous propionate, palladous benzoate, palladous chloride, palladous bromide, palladous oxide, etc., ruthenium acetate, etc., rhodium acetate, etc., platinous benzoate,

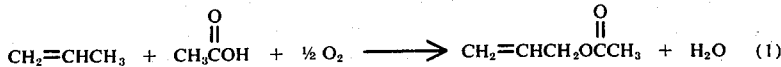

platinum dichloride, platinum oxide, etc., iridium chloride, etc., and the like and mixtures thereof.

The preferred catalyst is a mixture of the Group VIII noble metal and its salt. A more preferred catalyst is a mixture of palladium and palladous acetate.

A promoter may be added to the catalyst which influences activity and selectivity. Among the preferred promoters are the alkali metal and alkaline earth metal carboxylates, the transition metals, their salts, gold or copper.

The catalyst may be prepared in a number of different ways. For example, a neutral support such as carbon is impregnated with a palladium acetyl acetonate solution in benzene and dried. The resulting material is then impregnated with a solution of potassium acetate in water and dried. The catalyst is then treated with propylene, which reduces the palladium to the metallic state. The catalyst thus obtained contains palladium metal and potassium acetate in about 1:10 parts.

Varying amounts of the catalyst can be used within the scope of this invention. Amounts as low as about 0.1% based on weight of support have been found to be effective.

The working temperature is in the range of from about 100°C. to about 200°C. For optimum production of the allylic carboxylate, the temperature is in the range from about 125°C. to about 160°C. The working pressure is in the range from about atmospheric to about 150 psi. Somewhat higher or lower temperatures and pressures may, however, be used within the scope of the invention.

The oxygen in the instant process may be used in pure elementary form or in admixture with inert gases, for example, in the form of air. However, it is preferred to work with concentrated oxygen.

The olefin in the instant process may be used in pure form or in admixture with inert compounds, for example, saturated hydrocarbons.

The allylic ester formation is illustrated for the case of allyl acetate. A mixture of methyl acetate, water, acetic acid and methanol is passed through a bed of the catalyst in a tube reactor with propylene and oxygen at temperatures of from about 100°C. to about 160°C. at about 80 psi. Upon leaving the reaction zone, the products are condensed and a two phase mixture forms. The upper phase is a mixture of, in this case, methyl acetate, allyl acetate and methanol. The lower phase is principally water and methanol, with a small amount of allyl acetate. Direct distillation of the mixture affords the methanol and methyl acetate for recycle, leaving a two phase mixture of allyl acetate and water. The allyl acetate phase is decanted in a form suitable for further use.

The alkyl carboxylate ester hydrolysis mixture (derived from methyl acetate, for example) may be supplemented with more of the carboxylic acid (for example, acetic acid) with equally satisfactory results.

The present invention is also concerned with an improved overall process for the production of butanediol from propylene, which is based on the hydrolysis-oxidation sequence described above and is represented in equations 3-5:

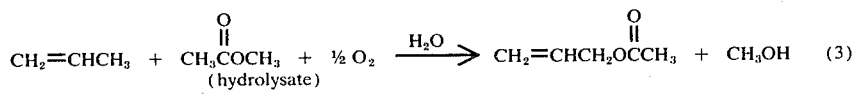

(3)

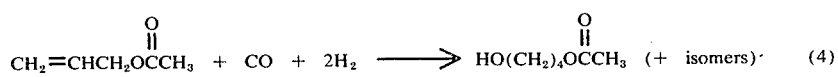

(4)

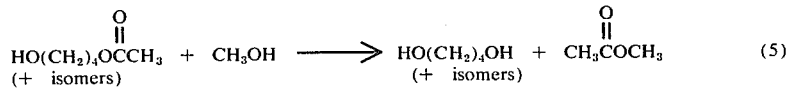

(5)

The methyl acetate formed in the methanolysis reaction (equation 5) can be recycled to the hydrolysis-oxidation step (equation 3). Preferably, the methyl acetate is isolated and recycled as its azeotrope with methanol.

Specifically, the improved process for the production of butanediol comprises: (a) reacting propylene and a mixture of methyl acetate, water, acetic acid and methanol with oxygen in the presence of a catalyst comprising a Group VIII noble metal, or its salts, or its oxides, or mixtures thereof to form allyl acetate; (b) converting the allyl acetate under hydroformylation-hydrogenation conditions to a mixture comprising the monoacetate esters of 1,4-butanediol, 2-methyl-1,3-propanediol and 1,2-butanediol and their respective diol and diacetate disproportionation products; (c) de-esterifying the mixture of the acetate esters of the butanediols so produced under methanolysis conditions to produce the corresponding butanediols and methyl acetate; (d) isolating the methyl acetate from the butanediols in a form suitable for use in (a).

For makeup of process losses, the methyl acetate may be supplemented with acetic acid in various proportions.

In copending application A, Ser. No. 365,228 of William E. Smith filed May 30, 1973 and assigned to the same assignee as the present invention, there is disclosed and claimed a process for making butanediols by reacting propylene, oxygen and a carboxylic acid to produce an allyl carboxylate which is then hydroformylated to produce the mixture of the corresponding aldehydes. Hydrogenation of the mixture produces a mixture of the esters of the corresponding diols. In copending application B, Ser. No. 365,231 of William E. Smith, filed May 30, 1973, and assigned to the same assignee as the present invention, there is disclosed and claimed a process wherein the hydrogenation is accomplished concurrently with the hydroformylation reaction. De-esterification of the diol ester mixture produces the desired butanediols which can be separated by distillation. These copending applications A and B are incorporated herein by reference.

The process of converting the allyl acetate under hydroformylation-hydrogenation conditions to a mixture comprising the monoacetate esters of 1,4-butanediol, 2-methyl-1,3-propanediol and 1,2-butanediol and their respective diol and diacetate disproportionation products, i.e., step (b) of the overall process of preparing 1,4-butanediol, is fully set forth in copending applications A and B described above, and incorporated herein by reference.

Methanolysis conditions that may be used in step (c) above are fully set forth in copending application C, Ser. No. 365,230, now abandoned, of Will Dockery Merritt, Jr., filed May 30, 1973 and copending application D, Ser. No. 365,239, now U.S. Pat. No. 3,880,939 of John E. Corn et al, filed May 30, 1973, both assigned to the same assignee as the present invention. Application C describes alcoholysis using a base catalyst while application D discloses alcoholysis in the presence of an acidic cationic exchange material. Applications C and D are incorporated herein by reference.

DESCRIPTION OF THE PREFERRED EMBODIMENT

The following Examples are set forth to illustrate more clearly the principal and practice of this invention to those skilled in the art. Unless otherwise specified, where parts or percents are mentioned, they are parts or percents by weight.

EXAMPLE 1

An 8 ft. × 1 inch diameter stainless steel tube is charged with one liter (1000 grams) of alumina catalyst (⅛ inch pellets, Harshaw Al-1802-E 1/8) and maintained at 250°C. while a mixture per hour of 910 grams of the methyl acetate-methanol azeotrope (composed of 740 grams of methyl acetate and 170 grams of methanol) and 900 grams of water is passed through under 80 psi pressure. The effluent contains, according to quantitative glpc analysis, 282 grams of acetic acid, 320 grams of methanol, 392 grams of methyl acetate, and 815 grams of water per hour. (The composition is essentially the same after a second pass, demonstrating that equilibrium has been reached.) These results indicate that for equation 6, K = 0.2 under these conditions.

$$CH_3\overset{O}{\overset{\|}{C}}OCH_3 + H_2O \rightleftharpoons CH_3\overset{O}{\overset{\|}{C}}OH + CH_3OH \qquad (6)$$

$$K = \frac{\left[CH_3\overset{O}{\overset{\|}{C}}OH\right]\left[CH_3OH\right]}{\left[CH_3\overset{O}{\overset{\|}{C}}OCH_3\right]\left[H_2O\right]} = 0.2$$

The hydrolysate is cooled to about 150°C. and mixed with (per hour) 2000 grams of propylene and 170 grams of oxygen. The resultant mixture is passed directly through a second 8 ft. × 1 inch diameter tube containing one liter of 4–8 mesh carbon impregnated with palladium (0.3%) and potassium acetate (3%), and operated at 160°C. and 80 psi pressure. The output per hour from this oxidation zone is a mixture (two liquid phases on cooling) composed of, according to quantitative glpc analysis, 355 grams of unconverted methyl acetate (48% recovery), 493 grams of allyl acetate (95% yield based on 52% conversion), 308 grams of methanol, a trace of acetic acid, and the excess water and propylene.

EXAMPLE 2

The tandem tube reactors are operated as described in Example 1, with the amount of water used per hour doubled to 1800 grams. Analysis of the condensed phases indicates the collection per hour of 229 grams of methyl acetate (31% unconverted), 644 grams of allyl acetate (93% yield based on 69% conversion), and 380 grams of methanol.

EXAMPLE 3

The tandem tube reactors are operated as in Example 1, with substitution of 740 grams per hour of pure methyl acetate for the methyl acetate-methanol azeotrope. Analysis of the condensed phases indicates the collection per hour of 254 grams of methyl acetate (34% unconverted), 607 grams of allyl acetate (92% yield based on 66% conversion) and 191 grams of methanol (90% yield).

EXAMPLE 4

The tandem tube reactors are operated as described in Example 2, with substitution of 740 grams per hour of pure methyl acetate for the methyl acetate-methanol azeotrope. Analysis of the condensed phases indicates the collection per hour of 157 grams of methyl acetate (21% unconverted), 705 grams of allyl acetate (89% yield based on 79% conversion), and 227 grams of methanol (90% yield).

EXAMPLE 5

A 6 inch × ¼ inch diameter stainless steel tube packed with an acidic ion exchange resin (Dowex 50 W × 8) is heated at 140°C. while a mixture per hour of 546 grams of the methyl acetate-methanol azeotrope (composed of 444 grams of methyl acetate and 102 grams of methanol) and 540 grams of water is passed through under 140 psi pressure. The mixture produced is the equilibrium hydrolysate (K = 0.2), suitable for use in the oxidation stage as described in Example 1.

EXAMPLE 6

A mixture of 740 grams of methyl acetate, 170 grams of methanol and 900 grams of water is combined with 25 grams of acidified aluminum silicate powder (Filtrol 20) and heated at 67°–72°C. for one hour. The catalyst is filtered off, leaving an equilibrium hydrolysate (K = 0.15) suitable for use in the oxidation stage as described in Example 1.

EXAMPLE 7

A miniplant is constructed and operated for the production of butanediol from propylene via the disclosed cyclic process. The tandem hydrolysis and oxidation tube reactors and basis procedure described in Example 1 are employed for the production of allyl acetate at the rate of about 500 grams per hour. The product stream of allyl acetate, methyl acetate, methanol, water and acetic acid forms two phases when condensed. The mixture is distilled directly using a conventional distilling column. The methyl acetate and methanol are taken overhead, leaving the allyl acetate, water and a small amount of acetic acid as the bottoms products. Distillation of the overhead affords the methyl acetate-methanol azeotrope (suitable for direct recycle in allyl acetate production) and methanol (suitable for use in the butanediol acetate methanolysis to be described). The allyl acetate-water-acetic acid distillation residue is cooled; the upper phase, essentially pure allyl acetate, is decanted and used directly in the next stage of the process. The aqueous phase contains about 5% of the allyl acetate, which can be recovered by distillation.

A two liter stirred autoclave heated at 125°C. is pressurized with 3000 psi of 2:1 hydrogen/carbon monoxide and charged with a mixture of 400 grams of the allyl acetate, 8.0 grams of cobalt octacarbonyl and 400 ml. of benzene. An exothermic reaction and gas uptake ensue. After 15 minutes at 125°–145°C., the product mixture is pumped from the autoclave, cooled and vented. It is then decobalted by heating at 110°C. for 10 minutes in a closed vessel, the addition of acetic acid being unnecessary because of its presence as a decomposition product. (The cobaltous acetate which forms is filtered off and transformed to cobalt octacarbonyl by subjection to hydrogen/carbon monoxide at elevated temperature and pressure ([160°C., 3000 psi]). The benzene solution is concentrated and the products are flash distilled, affording 474 grams (91% yield) of oxo aldehydes containing minor amounts of the butanediol acetate compounds. A glpc analysis indicates the presence of 4-acetoxybutyraldehyde, 3-acetoxy-2-methylpropionaldehyde and 2-acetoxybutyraldehyde in 7 : 1.5 : 1.5 ratio.

The aldehyde mixture is combined in a stirred autoclave with 50 grams of a 30% cobalt on silica catalyst, subjected to 1000 psi of hydrogen, and heated for 30 minutes at 150°C. Reduction to the diol derivatives is complete, in essentially quantitative yield.

After removal of the hydrogenation catalyst by filtration, the product mixture is examined by glpc and found to contain 4-acetoxybutanol, 3-acetoxy-2-methylpropanol and 2-acetoxybutanol, and small amounts of their respective diacetate and diol disproportionation products.

The low boiling components of the hydrogenation mixture (principally water, acetic acid and hydrogenation products derived from methacrolein and allyl acetate) are distilled off under reduced pressure. The residue is combined with 500 grams of methanol containing 2.5 grams of sodium hydroxide in a static mixer pipe leading to a 4 ft. × 1 inch diameter Goodloe distillation column. The methanolysis reaction takes place in a 2 ft. long packed section below the feed. Methyl acetate and most of the excess methanol are taken overhead and subsequently fractionated affording the methyl acetate-methanol azeotrope and pure methanol, both suitable for direct recycle.

The bottoms product contains, according to glpc analysis, 241 grams of 1,4-butanediol (67% yield in the conversion from allyl acetate), 14 grams of 2-methyl-1,3-propanediol (4% yield), and 51 grams of 1,2-butanediol (14% yield). The mixture is flash distilled, leaving a residue of partially deactivated catalyst. Fractionation of the diols through a 4 ft. × 2 inch diameter Goodloe column affords the three isomers — 1,4-butanediol (bp 144°/20 mm), 2-methyl-1,3-propanediol (bp 132°/20 mm), and 1,2-butanediol (bp 121°/20 mm).

The process as described is operated semi-continuously to provide butanediol at about 1 pound per hour.

Obviously, other modifications and variations of the present invention are possible in the light of the above teachings. It is therefore to be understood that changes may be made in the particular embodiments of the invention described which are within the full intended scope of the invention as defined by the appended claims.

What is claimed is:

1. A vapor process for preparing allylic esters of carboxylic acids which comprises reacting a mixture of lower alkyl carboxylate ester, water, and the corresponding carboxylic acid and alcohol with an olefin having an allylic carbon-hydrogen bond and oxygen in the presence of a catalyst consisting of a Group VIII noble metal, or its salts, or its oxides, or mixtures thereof and optionally a support and optionally a promoter selected from the group consisting of alkali metal carboxylates, alkaline earth metal carboxylates, the transition metals, their salts, gold or copper at a temperature of from about 100°C to about 200°C.

2. The process of claim 1 wherein the catalyst consists of a mixture of palladium and palladous acetate.

3. The process of claim 1 wherein the mixture of the lower alkyl carboxylate, water and the corresponding carboxylic acid and alcohol is at equilibrium.

4. A vapor phase process of preparing allyl acetate which comprises reacting propylene, a mixture of methyl acetate, water, acetic acid, and methanol and oxygen in the presence of a catalyst consisting of a Group VIII noble metal, or its salts, or its oxides, or mixtures thereof and optionally a support and optionally a promoter selected from the group consisting of alkali metal carboxylates, alkaline earth metal carboxylates, the transition metals, their salts, gold or copper at a temperature of from about 100°C. to about 160°C.

* * * * *

UNITED STATES PATENT OFFICE
CERTIFICATE OF CORRECTION

Patent No. 3,965,152　　　　　　　　　　Dated June 22, 1976

Inventor(s) William Edward Smith and R. John Gerhart

It is certified that error appears in the above-identified patent and that said Letters Patent are hereby corrected as shown below:

In claim 1, line 1, the word "phase" should be inserted between the words "vapor" and "process".

In claim 1, lines 2-3, the letter "a" should be inserted between the words "of" and "lower".

Signed and Sealed this

Ninth Day of November 1976

[SEAL]

Attest:

RUTH C. MASON
Attesting Officer

C. MARSHALL DANN
Commissioner of Patents and Trademarks